United States Patent [19]

Klingert et al.

[11] Patent Number: 4,963,470

[45] Date of Patent: Oct. 16, 1990

[54] TITANOCENES AND THEIR USE

[75] Inventors: Bernd Klingert, Inzlingen, Fed. Rep. of Germany; Franciszek Sitek, Therwil; Manfred Rembold, Aesch, both of Switzerland

[73] Assignee: Ciba-Geigy Corporation, Ardsley, N.Y.

[21] Appl. No.: 469,736

[22] Filed: Jan. 19, 1990

Related U.S. Application Data

[63] Continuation of Ser. No. 77,280, Jul. 24, 1987, abandoned.

[30] Foreign Application Priority Data

Aug. 1, 1986 [CH] Switzerland ............... 3100/86

[51] Int. Cl.$^5$ .................. G03C 1/70; C07F 7/08; C07F 7/18
[52] U.S. Cl. ................ 430/281; 430/194; 430/325; 430/925; 430/947; 526/126; 522/66; 522/29; 522/12; 544/64; 544/225; 546/2; 546/11; 546/12; 548/101; 556/11; 556/12; 556/53; 501/155; 501/152
[58] Field of Search ............. 430/194, 281, 325, 925, 430/947; 526/126; 522/66, 29, 12; 544/64, 225; 546/2, 11, 12; 548/101; 556/11, 12, 53; 501/155, 152, 522

[56] References Cited

U.S. PATENT DOCUMENTS

4,548,891 10/1985 Riediker et al. ............ 430/947 X
4,713,401 12/1987 Riediker et al. ............ 556/53 X
4,855,468 8/1989 Riediker et al. ............ 556/53

FOREIGN PATENT DOCUMENTS

207893 1/1987 European Pat. Off.

OTHER REFERENCES

Chemical Abstracts, vol. 106, No. 16, 1987, Columbus, Ohio, USA: Goodin: "Image-forming process," abstract No. 129330u (Abstract of European Patent Application 207893). Derwent Patent Reports, Derwent Publications Ltd., London, English Access Abstract No. 87-001568/01, of European Patent Application EP-207893-A, printed Jan. 7, 1987.

Primary Examiner—Marion C. McCamish
Assistant Examiner—Cynthia Hamilton
Attorney, Agent, or Firm—Luther A. R. Hall

[57] ABSTRACT

Titanocenes with silylated $\pi$-cyclopentadienyl ligands in which one or two carbo- or heterocyclic aromatic rings are bonded to the titanium, the aromatic rings being substituted by fluorine, $-CF_3$, $-C_2F_5$, $-CF_2CL$ or $-CF_2CH_3$ in at least one of the two ortho-positions relative to the metal-carbon bonds, are suitable as photoinitiators for the photopolymerization of ethylenically unsaturated substrates. They are distinguished by a high sensitivity, stability to air and the action of heat, and a high activity in the region of UV light to visible light. They are furthermore readily soluble in the photopolymerizable compositions.

23 Claims, No Drawings

TITANOCENES AND THEIR USE

This application is a continuation of application Ser. No. 077,280, filed 7/24/87, now abandoned.

The present invention relates to titanocenes with at least one aromatic radical containing a fluorine atom or at least one aromatic radical containing a fluoroalkyl group, a photopolymerizable composition of ethylenically unsaturated compounds containing these titanocenes as photoinitiators, a substrate coated with this composition and a process for the production of photographic relief images using this coated substrate.

It is known from European Patent No. A-0,122,223 and European Patent No. A-0,186,626 that titanocenes with fluoro- or fluoroalkylphenyl ligands are excellent photoinitiators. It has been found that substitution in the cyclopentadienyl radical reduces the photosensitivity of these titanocenes. The photosensitivity is furthermore influenced by the low solubility of these crystalline compounds in the components of the photosensitive compositions.

The present invention relates to titanocenes of the formula I

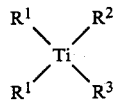 (I)

in which the two radicals $R^1$ independently of one another are cyclopentadienyl$^\ominus$ which is unsubstituted or substituted by $C_1$–$C_{18}$-alkyl, $C_2$–$C_{18}$-alkenyl, chlorine, phenyl or cyclohexyl, or the two radicals $R^1$ together are a substituted radical of the formula II

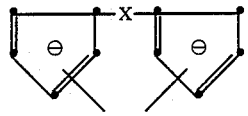 (II)

in which X is $(CH_2)_n$, where n=1, 2 or 3, alkylidene which has 2 to 12 C atoms and is unsubstituted or substituted by phenyl, or cycloalkylidene with 5 to 7 ring carbon atoms, $R^2$ is a 6-membered carbocyclic or 5- or 6-membered heterocyclic aromatic ring which is substituted by F, $CF_3$, $C_2F_5$, $CF_2Cl$ or $CF_2CH_3$ in at least one of the two ortho-positions relative to the metal-carbon bond, and furthermore can be substituted by one or more of the groups halogen, $C_1$–$C_{12}$-alkyl, $C_1$–$C_4$-alkoxy, $C_2$–$C_{10}$-alkoxycarbonyl and aminocarbonyl with up to 12 C atoms, or by a primary, secondary or tertiary amino or aminoalkyl group with up to 20 C atoms or a quaternary ammonium or ammoniumalkyl group with up to 30 C atoms, or, if $R^2$ is an aromatic ring substituted by F, this can be substituted by at least one polyoxaalkylene radical which is free or etherified or esterified, it being possible for this radical to be bonded to the aromatic ring either directly or via a bridge group, or $R^2$ and $R^3$ together are a radical of the formula III

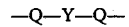 (III)

in which Q is a carbocyclic aromatic ring which is bonded to the titanium atom in the 2-position relative to the Y group and is substituted by fluorine in the 3-position, Y is methylene, $C_2$–$C_{12}$-alkylidene which is unsubstituted or substituted by phenyl, $C_5$–$C_7$-cycloalkylidene or a group —$NR^5$—, —O—, —S—, —SO—, —$SO_2$—, —CO—, —$SiR_2^4$— or —$SnR_2^4$— and and $R^5$ is hydrogen, $C_1$–$C_{12}$-alkyl, cyclohexyl, phenyl, tolyl or benzyl, and the radicals $R^4$ independently of one another are $C_1$–$C_{12}$-alkyl, cyclohexyl, phenyl or benzyl, $R^3$ has one of the meanings given for $R^2$ or is $C_2$–$C_{12}$-alkynyl, phenylalkynyl which has 2-5 C atoms in the alkyne radical and is unsubstituted or substituted by halogen or $C_1$–$C_4$-alkyl in the phenyl radical, or is a group —$SiR_3^4$, —$SnR_3^4$, in which the radicals $R^4$ are as defined above, —$N_3$ or —CN, or $R^3$ is additionally halogen, —NCO or NCS, if $R^2$ is an aromatic ring which is substituted by —$CF_3$, —$C_2F_5$, $CF_2Cl$ or $CF_3CH_3$, wherein, in these titanocenes, at least one radical $R^1$ is cyclopentadienyl$^\ominus$ which is substituted by at least one group of the formula IV or V $(R^6)_3Z$— (IV)

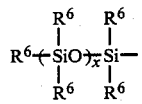 (V)

in which Z is Si or Ge, x is 1, 2 or 3 and each radical $R^6$ independently is linear or branched $C_1$–$C_{18}$-alkyl, $C_1$–$C_4$-halogenoalkyl, phenyl, $C_1$–$C_{18}$-alkoxy or $C_1$–$C_{18}$-alkoxymethyl.

In a preferred embodiment, in formula I one radical $R^1$ is unsubstituted cyclopentadienyl and the other radical $R^1$ contains up to 3 substituents, or each radical $R^1$ is substituted cyclopentadienyl, at least one substituent corresponding to the formula IV or V.

Preferred radicals $R^1$ are those radicals in which $R^1$ contains only substituents of the formula IV or V.

In formula V, x is preferably 1, and Z in formula IV is preferably Si.

$R^6$ is preferably $C_1$–$C_{18}$-alkyl, $C_1$–$C_4$-halogenoalkyl, $C_1$–$C_4$-alkoxy or phenyl. Examples of $R^6$ are methyl, ethyl, n- and i-propyl, n-, i- or t-butyl, pentyl, hexyl, 1,1,2,2-tetramethylethyl, heptyl, octyl, 2-ethyloctyl, nonyl, decyl, undecyl, dodecyl, tetradecyl, hexadecyl, octadecyl, chloromethyl, bromomethyl, 2-chloroethyl, methoxy, ethoxy, isopropoxy, butoxy and phenyl.

A preferred sub-group are those titanocenes in which, in formula IV, one radical $R^6$ is $C_1$–$C_{18}$-alkyl, $C_1$–$C_4$-halogenoalkyl, $C_1$–$C_4$-alkoxy or phenyl and the other two radicals $R^6$ are methyl. The group of the formula IV is particularly preferably a trimethylsilyl group. Further examples of radicals of the formula IV are triethylsilyl, ethyldimethylsilyl, n- or i-propyldimethylsilyl, tri-n-propylsilyl, n-, i- or t-butyldimethylsilyl, tri-n-butyl-silyl, tri-n-pentylsilyl, n-pentyl-dimethylsilyl, n-hexyl-dimethylsilyl, (1,1,2,2-tetramethylethyl)-dimethylsilyl, n-octyl-dimethylsilyl, n-decyldimethylsilyl, n-dodecyldimethylsilyl, n-octadecyldimethylsilyl and corresponding germyl radicals. Examples of radicals of the formula V are trimethylsiloxy-dimethylsilyl, phenyldimethylsiloxy-dimethylsilyl and butyldimethylsiloxy-dimethylsilyl.

Another preferred sub-group are those titanocenes in which one radical $R^1$ is a cyclopentadienyl anion which is substituted by groups of the formula IV or V and the other radical $R^1$ has the same meaning or is a cyclopentadienyl or methylcycloplentadienyl anion.

The two radicals $R^1$ in formula I are preferably identical radicals.

The aromatic radicals $R^2$ and $R^3$ are preferably each substituted by 2 fluorine atoms in the ortho-positions; or, preferably, by a $CF_3-$, $C_2F_5-$, $CF_2Cl-$ or $CF_2CH_3-$ group, especially if $R^3$ does not have the same meaning as $R^2$. Substitution with F and $CF_3$ is preferred.

$R^2$ in its meaning as a 6-membered carbocyclic aromatic and fluorine-substituted ring can be fluorinated indene, indane, fluorene, naphthalene or, in particular, phenyl. The two ortho-positions are preferably substituted by fluorine. Examples are: 4,6-difluoroinden-5-yl, 5,7-difluoroindan-6-yl, 2,4-difluorofluoren-3-yl, 1,3-difluoronaphth-2-yl and, in particular, 2,6-difluorophen-1-yl.

A heterocyclic aromatic 5-membered radical $R^2$ preferably contains one hetero atom and a 6-membered ring $R^6$ preferably contains 1 or 2 hetero atoms. Examples of such rings substituted by 2 fluorine atoms are: 2,4-difluoropyrr-3-yl, 2,4-difluorofur-3-yl, 2,4-difluorothiophen-3-yl, 2,4-difluoropyrid-3-yl, 3,5-difluoropyrid-4-yl and 4,6-difluoropyrimid-5-yl.

Examples of fluoroalkyl-substituted carbocyclic-aromatic rings $R^2$ are 4-(trifluoromethyl)inden-5-yl, 5,7-di(trifluoromethyl)indan-6-yl, 2-(trifluoromethyl)-fluoren-3-yl, 3-(trifluoromethyl)naphth-2-yl and, in particular, 2-(trifluoromethyl)phen-1-yl.

Examples of such fluoroalkyl-substituted heterocyclic-aromatic rings are: 2-(trifluoromethyl)pyrr-3-yl, 2-(trifluoromethyl)fur-3-yl, 2-(trifluoromethyl)thiophen-3-yl, 2-(trifluoromethyl)pyrid-3-yl, 3-(trifluoromethyl)pyrid-4-yl and 4-(trifluoromethyl)pyrimid-5-yl.

$R^2$ and $R^3$ together as a radical of the formula III can be, for example:

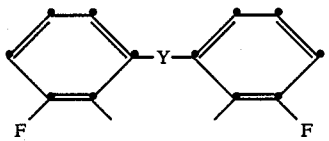

Y in formula III and in the above formula is preferably methylene, ethylidene, propylidene, $-S-$ or $-O-$.

$R^2$ can carry other substituents, such as halogen atoms, alkyl or alkoxy groups, alkoxycarbonyl or aminocarbonyl groups, amino groups or aminoalkyl groups and quaternization products thereof. Examples of such substituents are fluorine, chlorine, bromine, methyl, ethyl, iso-propyl, tert.-butyl, n-nonyl and n-dodecyl, methoxy, ethoxy and butoxy, methoxycarbonyl, ethoxycarbonyl, butoxycarbonyl, 2-ethylhexyloxy and n-decyloxy, aminocarbonyl, butylaminocarbonyl, diethylaminocarbonyl and pyrrolidinocarbonyl, $-NH_2$, $-NHC_4H_9$, $-N(CH_3)_2$, $-N(CH_3)_3^{\oplus}Cl^{\ominus}$, morpholino, piperidino, $-CH_2NH_2$, $-CH_2N(C_2H_5)_2$, $-CH_2N(C_2H_5)_3^{\oplus}Br^{\ominus}$ and pyrrolidinomethyl.

Alkyl $R^4$ preferably contains 1 to 6, in particular 1 to 4, C atoms and is, in particular, methyl.

In a preferred embodiment, $R^2$ and $R^3$ in formula I are identical and are a 6-membered carbocyclic or 5- or 6-membered heterocyclic aromatic ring which is substituted by F in one or both of the ortho-positions relative to the metal-carbon bond or by $CF_3$, $C_2F_5$, $CF_2Cl$ or $CF_2CH_3$ in one ortho-position and can contain other substituents as defined above. $R^2$ and $R^3$ in particular are 2,6-difluorophen-1-yl, which can contain 1 to 3 substituents as defined above.

In a preferred sub-group, $R^2$ and $R^3$ are a radical of the formula

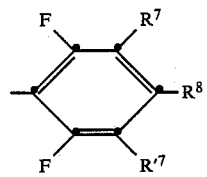

in which $R^7$, $R'^7$ and $R^8$ independently of one another are H, F, Cl or Br, or $R^7$ and $R'^7$ independently of one another are each H, F, Cl or Br, and $R^8$ is a primary, secondary or tertiary amino or aminoalkyl group with up to 20 C atoms or a quaternary ammonium or ammoniumalkyl group with up to 30 C atoms, or $R^8$ is a polyoxaalkylene radical which is free, esterified or etherified and is bonded to the phenyl ring directly or via a bridge group.

$R^2$ preferably contains at least one polyoxaalkylene radical which is free, etherified or esterified and is bonded to the aryl radical directly or via a bridge group. The polyoxaalkylene radical is preferably etherified with $C_1-C_{18}$-, in particular $C_1-C_{12}$- and especially $C_1-C_6$-alkyl or esterified with $C_1-C_{18}$-, in particular $C_1-C_{12}$- and especially $C_1-C_6$-acyl. Examples of alkyl are methyl, ethyl, n- and i-propyl, n-, i- and t-butyl, pentyl, hexyl, heptyl, octyl, nonyl, decyl, undecyl, dodecyl, tetradecyl, hexadecyl and octadecyl. Examples of acyl are formyl, acetyl, propionyl, trifluoroacetyl, butyryl, pentanoyl, hexanoyl, octanoyl, dodecanoyl and benzoyl. Etherified polyoxaalkylene radicals are preferred.

The polyoxaalkylene radical preferably contains 1 to 20, in particular 1 to 12 and especially 1 to 6 oxaalkylene units. The alkylene in the polyoxaalkylene radical preferably contains 2 to 6, in particular 2 to 4, C atoms and is, in particular, ethylene or 1,2-propylene. Other examples are 1,3-propylene, 1,2-, 1,3- and 1,4-butylene, pentylene and hexylene. The polyoxaalkylene radical can also contain various alkylene radicals.

In a preferred embodiment, the polyoxaalkylene radical corresponds to the formula $-C_zH_{2z}O)_oR^9$, in which z is a number from 2 to 6, o is a number from 1 to 20 to $R^9$ is H or $C_1-C_{18}$-alkyl.

If the polyoxaalkylene radical is bonded to the aromatic ring via a bridge group, the bridge groups can be, for example, one of the following groups: $-S-$, $-O-$, $-OSO_2-$, $-CH_2O-$, $-CH(CH_3)O-$, $-SO_2-$, $-C(O)O-$,

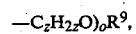

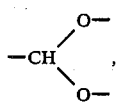

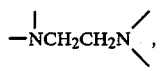

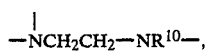

—NR$^{10}$CH$_2$CH$_2$NR$^{10}$—, —NCH$_2$CH$_2$NR$_2$$^{10}$, —CH$_2$N<, —CH$_2$NR$^{10}$—, —CH(COO—)$_2$, —CH$_2$COO—, —CONR$^{10}$—, —CH(CONR$^{10}$—)$_2$, —CH$_2$(CON<)$_2$, —CH$_2$CONR$^{10}$—, —CH$_2$CON<, —CON<, —OC(O)O—, —N(R$^{10}$)—COO—, —CH$_2$N(R$^{10}$)—COO—, —N(R$^{10}$)—CONH—, —CH$_2$N(R$^{10}$)—CONH—, —C$_n$H$_{2n}$OC(O)C$_m$H$_{2m}$O—, where n=0, 1 or 2 and m=1-6, —C$_n$H$_{2n}$OSiR$_{3-y}$$^{11}$O$_y$—, where n=0, 1 or 2 and y=1-3, —OCH$_2$CH$_2$OSiR$_{3-y}$$^{11}$O$_y$—, —COOSiR$_{3-y}$$^{11}$O$_y$— or —CH$_2$COOSiR$_{3-y}$$^{11}$O$_y$— where y=1-3, and in which R$^{10}$ is H, C$_1$-C$_{18}$-alkyl or C$_1$-C$_{18}$-acyl and R$^{11}$ is C$_1$-C$_{12}$-alkyl or phenyl.

In a preferred embodiment, R$^9$ is C$_1$-C$_{12}$-alkyl, R$^{10}$ is H or C$_1$-C$_{12}$-alkyl, R$^{11}$ is C$_1$-C$_6$-alkyl, z is a number from 2 to 4 and o is a number from 2 to 6.

In a particularly preferred group of the titanocenes according to the invention, the polyoxaalkylene radical bonded via a bridge group corresponds to the formula

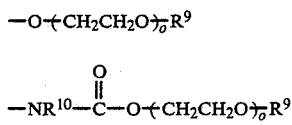

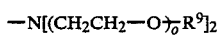

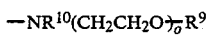

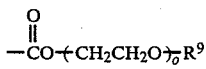

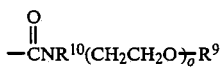

or

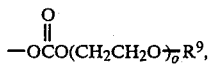

in which R$^9$ is C$_1$-C$_{12}$-alkyl, R$^{10}$ is H or C$_1$-C$_6$-alkyl and o is a number from 2 to 6.

Alkynyl R$^3$ preferably contains 2 to 6 C atoms. Examples are ethynyl, propynyl, butynyl, pentynyl and hexynyl. Phenylalkynyl R$^3$ is preferably substituted or unsubstituted phenylethynyl. Examples are (methylphenyl)-, (fluorophenyl)- and (chlorophenyl)alkynyl. R$^4$ in the (R$^4$)$_3$Si— and (R$^4$)$_3$Ge— groups preferably contains 1 to 4 C atoms and is, in particular, methyl. Examples of such groups have been mentioned above. Trimethylsilyl and trimethylgermyl are preferred.

A preferred group of titanocenes of the formula I are those in which R$^2$ is a radical of the formula

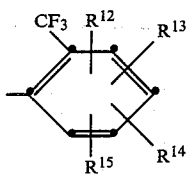

in which R$^{12}$, R$^{13}$, R$^{14}$ and R$^{15}$ independently of one another are hydrogen, —CF$_3$, bromine, chlorine or fluorine and R$^3$ has the meaning of R$^2$ or is halogen or —N$_3$, —CN, —NCO or —NCS. Amongst these, preferred titanocenes are those in which R$^{12}$, R$^{13}$ and R$^{14}$ are hydrogen and R$^{15}$ is in the ortho-position relative to the metal-carbon bond and is fluorine or hydrogen. R$^3$ in such fluoro-alkylated titanocenes is, in particular, F, Cl, Br, N$_3$, CN, NCO or NCS.

Examples of compounds of the formula I are: bis(R-cyclopentadienyl)-bis(pentafluorophenyl)-titanium, bis(R-cyclopentadienyl)-bis(3-bromo-tetrafluorophenyl)-titanium, bis(R-cyclopentadienyl)-bis(4-bromo-tetrafluorophenyl)-titanium, bis(R-cyclopentadienyl)-bis(3,5-dichloro-2,4,6-trifluorophenyl)-titanium, bis(R-cyclopentadienyl)-bis(4-morpholino-tetrafluorophenyl)-titanium, bis(R-cyclopentadienyl)-bis(4-[4'-methylpiperazino]-tetrafluorophenyl)-titanium, bis(R-cyclopentadienyl)-bis(2,4,6-trifluorophenyl)-titanium, bis(R-cyclopentadienyl)-bis(2,3,5,6-tetrafluorophenyl)-titanium, bis(R-cyclopentadienyl)-bis(2,3,6-trifluorophenyl)-titanium, bis(R-cyclopentadienyl)-bis(2,6-difluorophenyl)-titanium, bis(R-cyclopentadienyl)-bis(2,4,5-trifluorophenyl)-titanium, bis(R-cyclopentadienyl)-bis(2,3-difluorophenyl)-titanium, bis(R-cyclopentadienyl)-bis(2,5-difluorophenyl)-titanium, bis(R-cyclopentadienyl)-bis[2,3,5,6-tetrafluoro-4-(1',4'-dioxaoctylphenyl]-titanium, bis(R-cyclopentadienyl)-bis[2,3,5,6-tetrafluoro-4-(1',4',7'-trioxaoctylphenyl]-titanium, bis(R-cyclopentadienyl)-bis(2,6-difluoro-3-[1',4',7',10'-tetraoxadodecyl]-phenyl)-titanium, bis(R-cyclopentadienyl)-bis[2,6-difluoro-3-(1',4',7'-trioxahendecyl)-phenyl]-titanium, bis(R-cyclopentadienyl)-3,4,5,6,3',4',5',6'-octafluorodiphenyl sulphide 2,2'-diyl-titanium, bis(R-cyclopentadienyl)-(2-trifluoromethylphenyl)-titanium chloride or bromide or fluoride, bis(R-cyclopentadienyl)-bis(2-trifluoromethyl-phenyl)-titanium, bis(R-cyclopentadienyl)-(2-trifluoromethyl-6-fluorophenyl)-titanium fluoride, bis(R-cyclopentadienyl)-2,5-bis(trifluoromethyl)phenyl-titanium chloride, bis(R-cyclopentadienyl)-2-(trifluoromethyl)phenyl-titanium thiocyanate or isocyanate or cyanide, bis(R-cyclopentadienyl)-(2-trifluoromethyl-4-methoxyphenyl)-titanium chloride and bis(R-cyclopentadienyl)-bis(2-trifluoromethyl-4-tolyl)-titanium.

In these compounds, R is trimethylsilyl, trimethylgermyl, ethyldimethylsilyl, n- or t-butyldimethylsilyl, (1,1,2,2-tetramethylethyl)dimethylsilyl, hexyldimethylsilyl, octyldimethylsilyl or octadecyldimethylsilyl.

The titanocenes of the formula I can be prepared by known processes or analogous processes, for example by reacting 1 mol of a compound of the formula VI

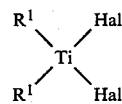 (VI)

in which $R^1$ is as defined in claim 1 and Hal is halogen, in particular chlorine, either with one mol of $LiR^2$ or $LiR^3$ and then with one mol of $LiR^3$ or $LiR^2$, or with 2 mol of $LiR^2$, $R^2$ and $R^3$ being as defined above.

The compounds of the formula VI are known in some cases or can be prepared by analogous processes, by reacting sodium cyclopentadienyl with compounds of the formula $(R^6)_3ZCl$ or $R^6(SiOR_2^6)_xSiR_2^6Cl$, reacting the resulting substituted cyclopentadienes with sodium again and then reacting 2 mol thereof with 1 mol of $Ti(Hal)_4$. If the two radicals $R^1$ are different, they are linked to the titanium analogously in 2 stages.

$R^2$- and $R^3$-halides, for example fluorides, chlorides and bromides, and the preparation of the corresponding lithium compounds are described in European Patent No. A-0,122,223 and European Patent No. A-0,186,626. The principle of the preparation of the titanocenes is also described there.

The compounds of the formula I according to the invention are usually crystalline orange-coloured compounds. Compounds in which the radical $R^2$ contains a polyoxaalkylene radical can also be liquid. The compounds of the formula I have a higher solubility than compounds without a silyl or germyl group, and the size of the silyl or germyl substituent does not impair the thermal and photochemical properties. Furthermore, the solubility can be influenced in a controlled manner by suitable choice of the $R^6$ radicals.

The compounds are stable when stored in the dark and can be handled without an inert gas. By themselves, they are outstandingly suitable as highly effective photoinitiators for photoinduced polymerization of ethylenically unsaturated compounds. They are distinguished here by a very high photosensitivity and activity over a wide wavelength range from about 200 nm (UV light) to about 600 nm. The titanocenes are furthermore also capable of effectively initiating polymerization under the influence of heat, heating to 170° C. to 240° C. being advantageous. The action of light and heating can of course also be utilized for polymerization, heating after exposure to light allowing lower temperatures, for example 80°–150° C., for the polymerization.

The present invention furthermore relates to a composition which can be polymerized by radiation and contains (a) at least one non-volatile monomeric, oligomeric or polymeric compound with at least one polymerizable ethylenically unsaturated double bond and (b) at least one titanocene of the formula I as a photoinitiator.

The compositions can contain further photoinitiators (c), for example those from the class of benzil ketals, 4-aroyl-1,3-dioxolanes, dialkoxyacetophenones, α-hydroxyacetophenones, α-aminoacetophenones or mixtures thereof. The weight ratio of these components (c):(b) can be, for example, from 1:1 to 30:1, preferably 5:1 to 15:1. The advantage is that the same or improved photosensitivities can be achieved with smaller amounts of titanocenes of the formula I.

The amount of the titanocenes according to the invention or their mixtures with other photoinitiators which is added essentially depends on economic viewpoints, their solubilities and on the desired sensitivity. In general, 0.01 to 20, preferably 0.05–10 and in particular 0.1 to 5% by weight is used, based on component (a).

Possible components (a) are those ethylenically unsaturated monomeric, oligomeric and polymeric compounds which react by photopolymerization to give higher molecular weight products and change their solubility in doing so.

Components which are particularly suitable are esters of ethylenically unsaturated carboxylic acids and polyols or polyepoxides, and polymers with ethylenically unsaturated groups in the chain or in side groups, for example unsaturated polyesters, polyamides and polyurethanes and copolymers thereof, polybutadiene and polybutadiene copolymers, polyisoprene and polyisoprene copolymers, polymers and copolymers with (meth)acrylic groups in side chains, and mixtures of one or more such polymers.

Examples of unsaturated carboxylic acids are acrylic acid, methacrylic acid, crotonic acid, itaconic acid, cinnamic acid and unsaturated fatty acids, such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, bisphenols, such as bisphenol A, and novolaks and resols. Examples of polyepoxides are those based on the polyols mentioned, in particular the aromatic polyols and epichlorohydrin. Polymers or copolymers which contain hydroxyl groups in the polymer chain or in side groups, for example polyvinyl alcohol and copolymers thereof or polymethacrylic acid hydroxyalkyl esters or copolymers thereof, are furthermore also suitable as the polyols. Other suitable diols are oligoesters with hydroxyl end groups.

Examples of aliphatic and cycloaliphatic polyols are alkylenediols with preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols with molecular weights of preferably 100 to 1,500, 1,3-cyclopentanediol, 1,2-, 1,3- or 1,4-cyclohexanediol, 1,4-dihydroxymethylcyclohexane, glycerol, tris-(β-hydroxyethyl)amine, trimethylolethane, trimethylolpropane, pentaerythritol, dipentaerythritol and sorbitol.

The polyols can be partly or completely esterified with one or various unsaturated carboxylic acids, it being possible for the free hydroxyl groups in part esters to be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, sorbitol tetramethacrylate, sorbitol pentaacrylate, sorbitol hexaacrylate, pentaerythritol modified triacrylate, an oligoester acrylate, an oligoester methacrylate, glycerol di- and triacrylate, 1,4- cyclohexane diacrylate, bisacrylates and bismethacrylates of polyethylene glycol with a molecular weight of 100-1,500, or mixtures thereof.

Suitable components (a) are also the amides of identical or different unsaturated carboxylic acids of aromatic, cycloaliphatic and aliphatic polyamines with preferably 2 to 6, in particular 2 to 4, amino groups. Examples of amines are alkylenediamines, such as ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di-(β-aminoethoxy)- or di(β-aminopropoxy)-ethane. Other suitable polyamines are polymers and copolymers with amino groups in the side chain and oligoamides with amino end groups.

Examples of such unsaturated amides are: methylene-bis-acrylamide, 1,6-hexamethylene-bis-acrylamide, diethylenetriamine-tris-methacrylamide, bis(methacrylamidopropoxy)ethane, β-methacryl-amidoethyl methacrylate and N[(β-hydroxyethoxy)ethyl]-acrylamide.

Suitable unsaturated polyesters and polyamides are derived, for example, from maleic acid and diols or diamines. The maleic acid can be replaced in part by other dicarboxylic acids. They can be used together with ethylenically unsaturated comonomers, for example styrene. The polyesters and polyamides can also be derived from dicarboxylic acids and ethylenically unsaturated diols or diamines, in particular from longer-chain compounds with, for example, 6 to 20 C atoms. Examples of polyurethanes are those which are built up from saturated or unsaturated diisocyanates and unsaturated or saturated diols.

Polybutadiene and polyisoprene and copolymers thereof are known. Examples of suitable comonomers are olefins, such as ethylene, propene, butene, hexene, (meth)acrylates, acrylonitrile, styrene and vinyl chloride. Polymers with (meth)acrylate groups in the side chain are also known. These can be, for example, reaction products of novolak-based epoxy resins with (meth)acrylic acid, homo- or copolymers of polyvinyl alcohol or hydroxyalkyl derivatives thereof esterified with (meth)acrylic acid, or copolymers of alkyl(meth)acrylates with hydroxyalkyl (meth)acrylates.

The photopolymerizable compounds can be used by themselves or as any desired mixtures. Mixtures of polyol (meth)acrylates are preferably used.

Binders can also be added to the compositions according to the invention, and this is particularly advantageous if the photopolymerizable compounds are liquid or viscous substances. The amount of binder can be, for example, 5-95, preferably 10-90 and in particular 50-90% by weight, based on the total composition. The binder is chosen according to the field of use and the properties required for this, such as the ease of developing in aqueous or organic solvent systems, adhesion to substrates and sensitivity to oxygen.

Examples of suitable binders are polymers with a molecular weight of about 5,000-2,000,000, preferably 10,000 to 1,000,000. Examples are: homo- and copolymeric acrylates and methacrylates, for example copolymers of methyl methacrylate/ethyl acrylate/methacrylic acid, poly(methacrylic acid alkyl esters), poly(acrylic acid alkyl esters), alkyl being $C_1$-$C_{20}$-alkyl, cellulose esters and ethers, such as cellulose acetate, cellulose acetobutyrate, methylcellulose and ethylcellulose, polyvinylbutyral, polyvinylformal, cyclized rubber and polyethers such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polyamides and polycaprolactams such as polycaprolactam and poly(hexamethyleneadipamide), and polyesters such as poly(ethylene glycol terephthalate) and poly(hexamethylene glycol succinate).

The compositions according to the invention are suitable as coating agents for all types of substrates, for example wood, paper, ceramics, plastics such as polyester and cellulose acetate films, and metals, such as copper and aluminium, on which a protective coating or a photographic image is to be applied by photopolymerization. The present invention furthermore relates to the coated substrates and a process for the application of photographic images to the substrates.

The coated substrates can be produced by applying a liquid composition, a solution or a suspension to the substrate. Liquid compositions without a solvent are preferred. It may be advantageous here for the titanocenes according to the invention to be used in the form of a liquid photoinitiator mixture containing other photoinitiators, for example a benzyl ketal, a 4-aroyl-1,3-dioxolane, a dialkoxy-acetophenone, an α-hydroxy- or α-amino-acetophenone or mixtures thereof, and a titanocene the formula I. Liquid mixtures of liquid to solid photoinitiators and liquid titanocenes, or liquid photoinitiators and syrupy to solid titanocenes, are particularly advantageous. These mixtures offer practical advantages and are distinguished by a high stability when stored in the dark.

Examples of benzil ketals are those of the formula

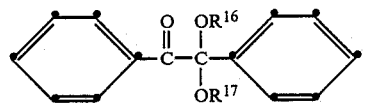

$R^{16} = R^{17} =$ —$CH_3$, —$CH_2CH_3$, —$(CH_2)_2CH_3$, —$(CH_2)_3CH_3$

—$CH_2CH_2CH(CH_3)_2$, —$CH_2$—$\underset{\underset{C_2H_5}{|}}{CH}$—$C_4H_9$, —$(CH_2)_9CH_3$, —$C_{10}H_{21}$-iso, —$C_{12}H_{25}$-n, —$C_9H_{19}$ to —$C_{11}H_{23}$ mixture,
—$C_{12}$-$C_{25}$ to —$C_{15}H_{31}$ mixture, —$CH_2CH$=$CH_2$,
—$CH(CH_3)CH$=$CH_2$, —$CH_2CH_2OC_3H_7$-iso, —$CH_2CH_2OC_4H_9$
—$CH_2CH_2OCH_2CH$=$CH_2$, —$CH(CH_3)$—$CH_2OC_4H_9$,
—$CH_2COOCH_3$, —$CH_2COOC_4H_9$, —$CH(CH_3)COOCH_3$,
—$CH_2CH_2COOC_2H_5$, —$CH(CH_3)CH_2COOCH_3$, —$CH_2CH_2CH(CH_3)OCH_3$, 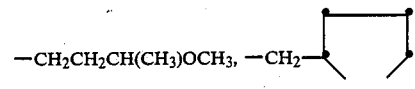

—$(CH_2CH_2O)_2CH_3$, —$(CH_2CH_2O)_2C_4H_9$, —$(CH_2CH_2O)_3CH_3$,
—$(CH_2CH_2O)_3C_2H_5$, —$(CH_2CH_2O)_3C_{12}H_{25}$,
—$(CH_2CH_2O)_5C_{10}H_{21}$, —$(CH_2CH_2O)_8C_9H_{19}$ to

—$C_{11}H_{23}$ (mixture), 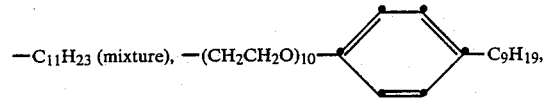

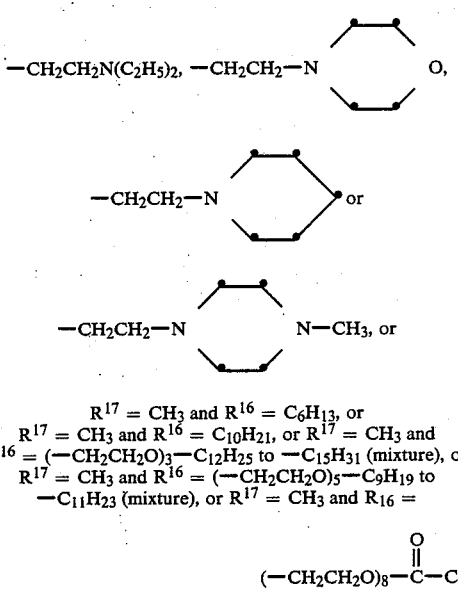

$R^{17} = CH_3$ and $R^{16} = C_6H_{13}$, or
$R^{17} = CH_3$ and $R^{16} = C_{10}H_{21}$, or $R^{17} = CH_3$ and
$R^{16} = (-CH_2CH_2O)_3-C_{12}H_{25}$ to $-C_{15}H_{31}$ (mixture), or
$R^{17} = CH_3$ and $R^{16} = (-CH_2CH_2O)_5-C_9H_{19}$ to
$-C_{11}H_{23}$ (mixture), or $R^{17} = CH_3$ and $R_{16} =$ $$(-CH_2CH_2O)_8-\overset{O}{\underset{\|}{C}}-C_{11}H_{23}.$$

Examples of 4-aroyl-1,3-dioxolanes are: 4-benzoyl-2,2,4-trimethyl-1,3-dioxolane, 4-benzoyl-4-methyl-2,2-tetramethylene-1,3-dioxolane, 4-benzoyl-4-methyl-2,2-pentamethylene-1,3-dioxolane, cis-trans-4-benzoyl-2,4-dimethyl-2-methoxymethyl-1,3-dioxolane, cis-trans-4-benzoyl-4-methyl-2-phenyl-1,3-dioxolane, 4-(4-methoxybenzoyl)-2,2,4-trimethyl-1,3-dioxolane, 4-(4-methoxybenzoyl)-4-methyl-2,2-pentamethylene-1,3-dioxolane, 4-(4-methylbenzoyl)-2,2,4-trimethyl-1,3-dioxolane, cis-trans-4-benzoyl-2-methyl-4-phenyl-1,3-dioxolane, 4-benzoyl-2,2,4,5,5-pentamethyl-1,3-dioxolane, cis-trans-4-benzoyl-2,2,4,5-tetramethyl-1,3-dioxolane, cis-trans-4-benzoyl-4-methyl-2-pentyl-1,3-dioxolane, cis-trans-4-benzoyl-2-benzyl-2,4-dimethyl-1,3-dioxolane, cis-trans-4-benzoyl-2-(2-furyl)-4-methyl-1,3-dioxolane, cis-trans-4-benzoyl-5-phenyl-2,2,4-trimethyl-1,3-dioxolane and 4-(4-methoxybenzoyl)-2,2,4,5,5-pentamethyl-1,3-dioxolane.

Examples of dialkoxyacetophenones are: α,α-dimethoxyacetophenone, α,α-diethoxyacetophenone, α,α-di-isopropoxyacetophenone, α,α-di-(2-methoxyethoxy)acetophenone, α-butoxy-α-ethoxyacetophenone, α,α-dibutoxy-4-chloroacetophenone, α,α-diethoxy-4-fluoroacetophenone, α,α-dimethoxy-4-methylacetophenone, α,α-dimethoxy-4-methylacetophenone, α,α-dimethoxypropiophenone, α,α-diethoxypropiophenone, α,α-diethoxybutyrophenone, α,α-dimethoxyisovalerophenone, α,α-diethoxy-α-cyclohexylacetophenone and α,α-dipropoxy-4-chloropropiophenone.

Examples of α-hydroxy-α-aminoacetophenones are: 2-hydroxy-2-methyl-1-phenyl-propan-1-one, 2-hydroxy-2-ethyl-1-phenylhexan-1-one, 1-(4-dodecylphenyl)-2-hydroxy-2-methylpropan-1-one, 1-(2,4-dimethylphenyl)-2-hydroxy-2-methylpropan-1-one, 2-hydroxy-1-(4-methoxyphenyl)-2-methylpropan-1-one, 2-hydroxy-2-methyl-1-phenylbutan-1-one, 1-benzoylcyclohexanol, 2-dimethylamino-2-methyl-1-phenylpropan-1-one, 2-dimethylamino-2-methyl-1-phenylpropan-1-one, 1-(4-fluorophenyl)-2-methyl-2-morpholinopentan-1-one, 2-methyl-1-(4-methylthiophenyl)-2-morpholinobutan-1-one, 2-dimethylamino-1-(4-methoxyphenyl)-2-methylpropan-1-one and 2-dimethylamino-1-(4-methoxyphenyl)-2-methylpropan-1-one.

The photoinitiator mixture (b)+(c) can be added in amounts of 0.5-20, preferably 1 to 10% by weight, based on component (a).

The choice of solvent and the concentration chiefly depend on the nature of the composition and on the coating process. The composition is applied uniformly to a substrate by means of known coating processes, for example by dipping, knife-coating, the curtain process, electrophoresis, brushing on, spraying or reverse roll coating. The amount applied (coating thickness) and the nature of the substrate (coating carrier) depend on the desired field of application. The coating carriers used are, for example, films of polyester, cellulose acetate or paper coated with plastic for photographic recording of information; specially treated aluminium for offset printing plates, and copper-lined laminates for the production of printed circuits. The coating thicknesses for photographic materials and offset printing plates are in general about 0.5 to about 10 μm; and for printed circuits they are in general 1 to about 100 μm. If solvents are also used, these are removed after coating.

Photocurable compositions such as are used for the various purposes usually contain a number of other additives in addition to the photopolymerizable compounds and the photoinitiators. It is therefore often usual to add thermal inhibitors which are intended to protect the components from premature polymerization, especially during preparation of the compositions by mixing. Examples of compounds which are used for this are hydroquinone, hydroquinone derivatives, p-methoxyphenol, β-naphthols or sterically hindered phenols, for example 2,6-di(tert.-butyl)-p-cresol. Small amounts of UV absorbers, for example those of the benzotriazole, benzophenone or oxalanilide type, can furthermore be added. Photostabilizers of the sterically hindered amine type (HALS) can also be added.

Copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine, can be added to increase the stability to storage in the dark.

Paraffin or similar waxy substances are frequently added to photocurable mixtures in order to exclude the inhibiting effect of atmospheric oxygen. These substances float out when polymerization starts because of a lack of solubility in the polymer and form a transparent surface layer which prevents access of air.

Other customary additives are photosensitizers which absorb in certain wavelengths and transmit the absorbed energy to the initiators or themselves function as an additional initiator. Examples of these are in particular thioxanthone, anthracene, anthraquinone and coumarin derivatives.

Other customary additives are accelerators of the amine type which are of particular importance in pigmented formulations, since they act as chain transfer agents. Examples of these are N-methyldiethanolamine, triethylamine, ethyl p-dimethylaminobenzoate and Michler's ketone. The effect of the amines can be intensified by addition of aromatic ketones of the benzophenone type.

Other customary additives are fillers, pigments, dyes and processing auxiliaries, for example adhesives, wetting agents and flow control agents.

Photocuring is of great importance for printing inks, since the drying time of the binder is a decisive factor for the rate of production of graphic products and should be of the order of fractions of seconds. UV-curable printing inks are of particular importance for screen printing.

The photocurable compositions according to the invention are also particularly suitable for the production of printing plates, in particular flexographic printing plates. For this, for example, mixtures of soluble linear polyamides or of styrene/butadiene rubber with photopolymerizable monomers, for example acrylamides or acrylates, and a photoinitiator are used. Films and plates of these systems (wet or dry) are exposed via the negative (or positive) of the printing master and the non-cured portions are then eluted with a solvent.

Another field of use for photocuring is coating metals, for example the varnishing of sheet metal for tubes, cans or bottle caps, and photocuring of coatings of plastic, for example PVC-based floor or wall coverings.

Examples of photocuring of coatings on paper are colourless varnishing of labels, record sleeves or book jackets.

The use of photocurable compositions for imaging processes and for optical production of information carriers is also important. Here, the layer (wet or dry) applied to the carrier is irradiated with light of short wavelength through a photomask and the non-exposed areas of the coating are removed by treatment with a solvent (=developer). The exposed areas are cross-linked-polymeric and are therefore insoluble and remain on the carrier. On appropriate staining, visible images result. If the carrier is a metallized layer, after exposure and development the metal can be etched away from the non-exposed areas or thickened by electroplating. Printed circuits and photoresists can be produced in this manner.

Light sources with a high content of light of short wavelength are suitable for the exposure. Appropriate technical devices and various types of lamps are currently available for this. Examples are carbon arc lamps, xenon arc lamps, mercury vapour lamps, metal halogen lamps, fluorescent lamps, argon lamps or photographic floodlights. Laser light sources have also recently been used. These have the advantage that no photomasks are necessary; the controlled laser beam writes directly onto the photocurable layer.

The following examples illustrate the invention in more detail.

PREPARATION EXAMPLES

EXAMPLES 1-7

64.4 ml of a 1.6 molar butyllithium hexane solution (103 mmol) are added dropwise to a solution of 17.3 g of pentafluorobenzene (103 mmol) in 500 ml of absolute diethyl ether at $-70°$ C. under argon and the mixture is stirred at $-70°$ C. for one hour. 17.7 g of $(Me_3SiCp)_2TiCl_2$ (50 mmol) are then added in one portion and the reaction mixture is warmed slowly to room temperature and stirred at room temperature for a further three hours. Thereafter, the mixture is filtered and the residue is extracted several times with ether. The combined filtrates are evaporated in vacuo and the orange-red solid which remains is chromatographed with ether over aluminium oxide (Woelm, neutral). The orange-coloured eluate is concentrated at room temperature until saturated and then cooled to $-78°$ C. The orange-coloured crystals of $(Me_3SiCp)_2Ti(C_6F_5)_2$ which form are dried under a high vacuum. Yield: 23.6 g (72%).

An analogous procedure is followed in Examples 2-7. Chromatography and crystallization of the products in Examples 5-7 is with a mixture of ether/hexane=1:1.

The reaction conditions and results are summarized in Tables 1 and 2. In these, Cp is cyclopentadienyl and Me is methyl. All the products are orange-coloured and are stable in air under exclusion of light.

TABLE 1

| | | Educts | | |
|---|---|---|---|---|
| Example | Titanium compound | Fluoroaromatic | 1.6 m butyllithium in hexane | Solvent |
| 1 | $(Me_3SiCp)_2TiCl_2$ 17.7 g | $C_6F_5H$ 17.3 g | 64.4 ml | ether 500 ml |
| 2 | $(Me_3SiCp)CpTiCl_2$ 16.1 g | $C_6F_5H$ 17.3 g | 64.4 ml | ether 500 ml |
| 3 | $(Me_3SiCp)_2TiCl_2$ 5.9 g | 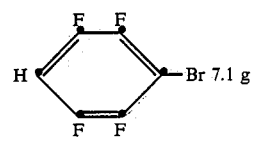 Br 7.1 g | 19.4 ml | ether 150 ml |
| 4 | $(Me_3SiCp)_2TiCl_2$ 5.9 g | 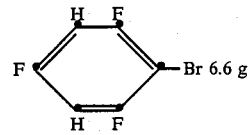 Br 6.6 g | 19.4 ml | ether 150 ml |
| 5 | $(Me_3SiCp)CpTiCl_2$ 3.2 g | Br 5.3 g | 15.6 ml | ether 100 ml |

TABLE 1-continued

| | | Educts | | |
|---|---|---|---|---|
| Example | Titanium compound | Fluoroaromatic | 1.6 m butyllithium in hexane | Solvent |
| 6 | (Me₃SiCp)₂TiCl₂ 5.9 g | o-Br-C₆H₄-CF₃ 3.6 g | 10.0 ml | ether 150 ml |
| 7 | (Me₃SiCp)CpTiCl₂ 9.6 g | o-Br-C₆H₄-CF₃ 6.9 g | 19.4 ml | ether 300 ml |

TABLE 2

| | | Products | | | |
|---|---|---|---|---|---|
| | | | | Analysis % Ti | |
| Example | Formula | Yield % | Melting point/°C. | calculated | found |
| 1 | (Me₃Sicp)₂Ti(C₆F₅)₂ | 72 | 190 | 7.30 | 7.27 |
| 2 | (Me₃Sicp)cpTi(C₆F₅)₂ | 80 | 175 | 8.20 | 8.09 |
| 3 | (Me₃Sicp)₂Ti(p-HC₆F₄)₂ | 50 | 150 | 7.72 | 7.76 |
| 4 | (Me₃Sicp)₂Ti(2,4,6-F₃C₆H₂)₂ | 53 | 146 | 8.19 | 8.02 |
| 5 | (Me₃Sicp)cpTi(2,4,6-F₃C₆H₂)₂ | 59 | 175 | 9.35 | 9.08 |
| 6 | (Me₃Sicp)₂Ti(o-CF₃C₆H₄)Cl | 44 | 111 | 9.52 | 9.55 |
| 7 | (Me₃Sicp)cpTi(o-CF₃C₆H₄)Cl | 67 | 61 | 11.12 | 10.90 |

EXAMPLES 8–24

The particular amount of fluoroaromatic stated in Table 3 is dissolved in the particular solvent, under argon, the corresponding amount of a 1.6 molar butyllithium-hexane solution is added dropwise at −70° C., and the mixture is stirred at −70° C. for a further hour. The stated amount of titanocene dichloride is then added in one portion, and the reaction mixture is warmed slowly to room temperature and stirred at room temperature for a further three hours. Thereafter, it is completely evaporated in vacuo, the residue is extracted with methylene chloride or chloroform, and the extracts are filtered. The filtrate is evaporated again, and the residue which remains is purified as stated in Table 4.

The products are yellow-orange to red-orange in colour. With the exception of Example 21, which is an oil, the products are crystalline. All the products are stable under exclusion of light and are not sensitive to air.

In the following tables, Cp is cyclopentadienyl, Ph is phenyl and Me is methyl. Chromatographic purification is carried out on columns of aluminium oxide (Woelm), neutral (=Al₂O₃) or silica gel 60 (Merck) (=SiO₂).

TABLE 3

| | | Educts | | |
|---|---|---|---|---|
| Ex. | Titanium compound | Fluoroaromatic | 1.6 m butyl-lithium in hexane | Solvent |
| 8 | [(Me₃Si)₂Cp]CpTiCl₂ 7.9 g | pentafluorobenzene 6.9 g | 26.2 ml | ether 250 ml |
| 9 | [(Me₃Si)₃Cp]CpTiCl₂ 9.4 g | pentafluorobenzene 6.7 g | 26.2 ml | ether 250 ml |
| 10 | [(n-C₆H₁₃)₃SiCp]₂TiCl₂ 5.0 g | pentafluorobenzene 2.1 g | 8.0 ml | ether 120 ml |
| 11 | (n-C₈C₁₇SiMe₂Cp)CpTiCl₂ 8.4 g | pentafluorobenzene 6.9 g | 26.2 ml | ether 200 ml |
| 12 | (n-C₈H₁₇SiMe₂Cp)₂TiCl₂ 10.0 g | pentafluorobenzene 5.7 g | 21.9 ml | ether 170 ml |
| 13 | [(n-C₈H₁₇SiMe₂)₂TiCl₂ 11.8 g | pentaflurorbenzene 6.7 g | 25.6 ml | ether 200 ml |
| 14 | [(n-C₁₈H₃₇SiMe₂Cp)₂TiCl₂ 4.3 g | pentafluorobenzene 1.7 g | 6.4 ml | ether 50 ml |
| 15 | (SiMe₂Cp)₂TiCl₂ 10.7 g | pentafluorobenzene 6.9 g | 26.2 ml | ether 200 ml |
| 16 | (ClCH₂SiMe₂Cp)₂TiCl₂ 4.6 g | pentafluorobenzene 3.4 g | 12.5 ml | ether 150 ml |
| 17 | (Ph₃SiCp)₂TiCl₂ 5.6 g | pentafluorobenzene 2.5 g | 7.1 ml | ether 100 ml |
| 18 | [(C₂H₅O)₃SiCp ₂TiCl₂ 12.0 g | pentafluorobenzene 8.5 g | 32.8 ml | ether 250 ml |
| 19 | (Me₃SiOSiMe₂Cp)₂TiCl₂ 0.9 g | pentafluorobenzene 0.6 g | 2.1 ml | ether 20 ml |
| 20 | (Me₃SiCp)MeCpTiCl₂ 6.7 g | pentafluorobenzene 6.7 g | 25.0 ml | ether 200 ml |
| 21 | (Me₃SiCp)₂TiCl₂ 7.9 g | Cl-C₆F₄-O-(CH₂CH₂O)₂C₄H₉ 13.8 g | 25.0 ml | ether 200 ml |
| 22 | (Me₃SiCp)₂TiCl₂ 7.9 g | m-difluorobenzene 4.7 g | 26.2 ml | THF 200 ml |
| 23 | (Me₃SiCp)CpTiCl₂ 5.8 g | m-difluorobenzene 4.7 g | 26.2 ml | THF 200 ml |

TABLE 3-continued

| | | Educts | | |
|---|---|---|---|---|
| Ex. | Titanium compound | Fluoroaromatic | 1.6 m butyl-lithium in hexane | Solvent |
| 24 | [(Me$_3$Si)$_2$Cp]CpTiCl$_2$ 7.1 g | m-difluorobenzene 4.6 g | 26.2 ml | THF 200 ml |

TABLE 4

| | Products | | |
|---|---|---|---|
| Ex. | Formula | Purification | m.p./°C. |
| 8 | [(Me$_3$Si)$_2$Cp]CpTi(C$_6$F$_5$)$_2$ | chromatography (Al$_2$O$_3$, ether) | 162 |
| 9 | [(Me$_3$Si)$_3$Cp]CpTi(C$_6$F$_5$)$_2$ | chromatography (Al$_2$O$_3$, hexane:ether = 9:1) | 166 |
| 10 | [(n-C$_6$H$_{13}$)$_3$SiCp]$_2$Ti(C$_6$F$_5$)$_2$ | chromatography (SiO$_2$, hexane) | 75 |
| 11 | (n-C$_8$H$_{17}$SiMe$_2$Cp)CpTi(C$_6$F$_5$)$_2$ | chromatography (Al$_2$O$_3$, hexane:ether = 8:2) | 92 |
| 12 | (n-C$_8$H$_{17}$SiMe$_2$Cp)$_2$Ti(C$_6$F$_5$)$_2$ | chromatography (Al$_2$O$_3$, hexane) | 76 |
| 13 | [(n-C$_8$H$_{17}$SiMe$_2$)$_2$Cp]CpTi(C$_6$F$_5$)$_2$ | chromatography (Al$_2$O$_3$, hexane:ether = 9:1) | 61 |
| 14 | (n-C$_{18}$H$_{37}$SiMe$_2$Cp)$_2$Ti(C$_6$F$_5$)$_2$ | chromatography (SiO$_2$, hexane) | 66 |
| 15 | ((CH$_3$)CHC(CH$_3$)—SiMe$_2$Cp)$_2$Ti(C$_6$F$_5$)$_2$ | chromatography (Al$_2$O$_3$,hexane) | 186 |
| 16 | (ClCH$_2$SiMe$_2$Cp)$_2$Ti(C$_6$F$_5$)$_2$ | recrystallization (hexane) | 161 |
| 17 | (Ph$_3$SiCp)$_2$Ti(C$_6$F$_5$)$_2$ | recrystallization (CH$_2$Cl$_2$/hexane) | 216 |
| 18 | [(C$_2$H$_5$O)$_3$SiCp]Ti(C$_6$F$_5$)$_2$ | recrystallization (pentane) | 78 |
| 19 | (Me$_3$SiOSiMe$_2$Cp)$_2$Ti(C$_6$F$_5$)$_2$ | chromatography (SiO$_2$, hexane) | 136 |
| 20 | (Me$_3$SiCp)MeCpTi(C$_6$F$_5$)$_2$ | recrystallization (ether:hexane = 1:3) | 159 |
| 21 | (Me$_3$SiCp)$_2$Ti[−C$_6$F$_4$−O(CH$_2$CH$_2$O)$_2$C$_4$H$_9$]$_2$ | chromatography (SiO$_2$, hexane:ether = 10:1) | oil |
| 22 | (Me$_3$SiCp)$_2$Ti[−C$_6$H$_2$F$_3$−]$_2$ | chromatography (Al$_2$O$_3$, hexane:ether = 1:1) | 153 |
| 23 | (Me$_3$SiCp)CpTi[−C$_6$H$_3$F$_2$−]$_2$ | chromatography (Al$_2$O$_3$, hexane:ether = 1:1) | 174 |
| 24 | [(Me$_3$Si)$_2$Cp]CpTi[−C$_6$H$_3$F$_2$−]$_2$ | chromatography (Al$_2$O$_3$, hexane:ether = 9:1) | 105 |

EXAMPLE 25

Photocuring of an acrylate mixture

A photocurable composition is prepared by mixing the following components: 50 parts of an oligourethane acrylate (Actilan ® AJ 20, SNPE, France), 20 parts of trimethylolpropane triacrylate, 15 parts of tripropylene glycol diacrylate, 15 parts of N-vinylpyrrolidone and 0.5 part of a silicone-based flow control agent (BYK ® 300, Byk-Mallinckrodt, FRG).

Portions of this composition are mixed with the amount of photoinitiator or initiator mixtures stated in the following table. The initiator mixtures are solutions of a titanocene in a liquid initiator of the ketal type of the formula A

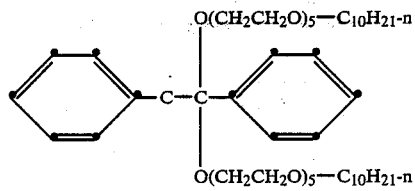

All the operations are carried out under red light or yellow light.

The samples to which initiator has been added are applied in a thickness of 100 μm to aluminium sheets (10×15 cm). A 76 μm thick polyester film is placed on the liquid layer, and a standardized test negative with 21 steps of different optical density (Stauffer wedge) is placed on this. A second polyester film is placed on top, and the laminate thus obtained is fixed on a metal plate. The sample is then exposed with a 5 KW metal halide lamp at a distance of 30 cm, for 5 seconds in a first test series, 10 seconds in a second test series and 15 seconds in a third test series. After the exposure, the films and the mask are removed, the exposed layer is developed in an ethanol bath for 15 seconds, and the specimens are then dried at 60° C. for 5 minutes. The sensitivity of the initiator system used is characterized by stating the last wedge step imaged without tackiness. The higher the number of the steps, the more sensitive the system. An increase by two steps means an approximate doubling of the rate of curing. The results are shown in Table 5.

TABLE 5

| Titanocene initiator | Ketal initiator | Number of steps imaged after exposure | | |
|---|---|---|---|---|
| | | 5 seconds | 10 seconds | 15 seconds |
| 0.2% of Example 1 | — | 12 | 14 | 16 |
| 0.2% of Example 1 | 1.8% of A | 12 | 14 | 16 |
| 0.2% of Example 3 | — | 11 | 13 | 15 |
| 0.2% of Example 3 | 1.8% of A | 13 | 15 | 17 |
| 0.2% of Example 4 | — | 12 | 14 | 16 |
| 0.2% of Example 4 | 1.8% of A | 12 | 14 | 16 |
| 0.2% of Example 5 | — | 13 | 15 | 17 |
| 0.2% of Example 5 | 1.8% of A | 14 | 16 | 17 |
| 0.2% of Example 6 | — | 8 | 10 | 11 |
| 0.2% of Example 6 | 1.8% of A | 8 | 10 | 12 |

EXAMPLE 26

Photocuring of an acrylate mixture

The following components are mixed: 50 parts of an oligourethane acrylate (Actilan ® 20, SNPE, France), 10 parts of trimethylolpropane triacrylate, 10 parts of dipentaerythritol pentaacrylate, 15 parts of tripropylene glycol diacrylate, 15 parts of N-vinylpyrrolidone and 0.30 part of silicone-based flow control agent (BYK ® 300, Byk-Mallinckrodt, FRG).

The photoinitiators shown in Table 6 are then added. The liquid ketal A defined in Example 25 is used as a coinitiator.

The samples to which initiator has been added are applied in a coating thickness of 100 μm to aluminium foil (200 μm) and the specimens are exposed under a 21-step Stauffer wedge as described in Example 25. After exposure of in each case 5, 10 and 20 seconds, the samples are developed with ethanol in an ultrasonic bath for 10 seconds and then dried. The highest step which is developed completely and without tackiness is shown in Table 6.

TABLE 6

| Titanocene initiator | Ketal initiator | Number of steps imaged after exposure | | |
|---|---|---|---|---|
| | | 5 seconds | 10 seconds | 20 seconds |
| 0.2% of Example 8 | — | 10 | 13 | 15 |
| 0.2% of Example 8 | 1.8% of A | 11 | 14 | 15 |
| 0.2% of Example 9 | — | 8 | 10 | 12 |
| 0.2% of Example 9 | 1.8% of A | 8 | 10 | 12 |
| 0.2% of Example 10 | — | 6 | 8 | 10 |
| 0.2% of Example 10 | 1.8% of A | 8 | 10 | 12 |
| 0.2% of Example 11 | — | 11 | 14 | 15 |
| 0.2% of Example 11 | 1.8% of A | 12 | 15 | 16 |
| 0.2% of Example 12 | — | 8 | 11 | 12 |
| 0.2% of Example 12 | 1.8% of A | 8 | 11 | 12 |
| 0.2% of Example 13 | — | 10 | 13 | 16 |
| 0.2% of Example 13 | 1.8% of A | 11 | 13 | 16 |
| 0.2% of Example 14 | — | 5 | 7 | 9 |
| 0.2% of Example 14 | 1.8% of A | 7 | 9 | 13 |
| 0.2% of Example 15 | — | 8 | 10 | 12 |
| 0.2% of Example 15 | 1.8% of A | 9 | 11 | 13 |
| 0.2% of Example 18 | — | 11 | 13 | 15 |
| 0.2% of Example 18 | 1.8% of A | 11 | 13 | 15 |
| 0.2% of Example 22 | — | 11 | 14 | 15 |
| 0.2% of Example 22 | 1.8% of A | 11 | 14 | 15 |
| 0.2% of Example 23 | — | 12 | 15 | 16 |
| 0.2% of Example 23 | 1.8% of A | 13 | 15 | 17 |
| 0.2% of Example 24 | — | 11 | 14 | 15 |
| 0.2% of Example 24 | 1.8% of A | 12 | 14 | 16 |

EXAMPLE 27

A composition is prepared from: 150 parts of a 30% solution of a styrene-monomethyl maleate copolymer (Scripset ® 540, Monsanto Chem., USA) is acetone, 48 parts of trimethylolpropane triacrylate, 7 parts of polyethylene glycol diacrylate and 0.08 part of crystal violet.

Samples of this were prepared by admixing 0.3% of the titanocene initiators listed in Table 7 and 1.7% of coinitiator B. This consists of 50% of the α-hydroxyactophenone B'

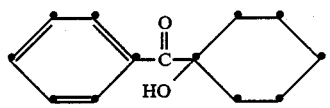

and 50% of benzophenone.

The samples are applied in a coating thickness of 50 μm to aluminium foils, corresponding to a dry coating thickness of about 50 μm. Exposure under a 21-step wedge is effected as described in Example 25. Development is carried out in a developer bath with the following composition: 15 parts of sodium metasilicate, 0.16 part of potassium hydroxide, 3 parts of polyethylene glycol 6000, 0.5 part of levulinic acid and 1,000 parts of water.

Table 7 shows the maximum number of steps imaged after exposure for 20, 40 and 60 seconds.

TABLE 7

| Titanocene initiator | Ketal initiator | Number of steps imaged after exposure | | |
|---|---|---|---|---|
| | | 5 seconds | 10 seconds | 15 seconds |
| 0.2% of Example 16 | — | 14 | 16 | 19 |
| 0.2% of Example 16 | 1.7% of B | 13 | 15 | 18 |
| 0.2% of Example 17 | — | 10 | 12 | 14 |
| 0.2% of Example 17 | 1.7% of B | 10 | 12 | 13 |
| 0.2% of Example 19 | — | 14 | 16 | 19 |
| 0.2% of Example 19 | 1.7% of B | 12 | 17 | 19 |
| 0.2% of Example 20 | — | 15 | 18 | 21 |

TABLE 7-continued

| Titanocene initiator | Ketal initiator | Number of steps imaged after exposure | | |
|---|---|---|---|---|
| | | 5 seconds | 10 seconds | 15 seconds |
| 0.2% of Example 20 | 1.7% of B | 14 | 16 | 18 |
| 0.2% of Example 21 | — | 13 | 15 | 17 |
| 0.2% of Example 21 | 1.7% of B | 16 | 16 | 17 |

EXAMPLE 28

A photocurable composition is prepared by mixing the following components: 47.3 parts of a thermoplastic polyacrylate with carboxyl groups (Carbose ® 525, B.F. Goodrich, USA), 10.7 parts of hexamethoxymethylmelamine, 37.7 parts of pentaerythritol triacrylate and 4.3 parts of polyvinylpyrrolidone.

0.5 g of Irgalithgrün ® GLN (Ciba-Geigy AG) is added to 100 g of this composition, and the mixture is diluted with 30 g of methanol and 319 g of methylene chloride.

Samples of this solution are prepared by addition of 0.3% of the titanocene initiators listed in Table 8 and 1.7% of the liquid ketone initiator mixture B (see Example 27), in each case based on the solids contained in the solution.

The samples are applied in a wet coating thickness of 200 μm (~45 μm dry coating thickness) to a 200 μm thick aluminium foil, and the solvent is evaporated off at 60° C./15 minutes. Exposure under the step wedge is carried out as described in Example 25. The exposed samples are developed in an ultrasonic bath with the alkaline developer solution described in Example 27. Table 8 shows the maximum number of steps imaged after exposure for 20, 40 and 60 seconds.

TABLE 8

| Titanocene initiator | Ketal initiator | Number of steps imaged after exposure | | |
|---|---|---|---|---|
| | | 5 seconds | 10 seconds | 15 seconds |
| 0.3% of Example 16 | — | 14 | 16 | 20 |
| 0.3% of Example 16 | 1.7% of B | 13 | 15 | 17 |
| 0.3% of Example 17 | — | 12 | 14 | 16 |
| 0.3% of Example 17 | 1.7% of B | 12 | 15 | 17 |
| 0.3% of Example 19 | — | 13 | 14 | 20 |
| 0.3% of Example 19 | 1.7% of B | 13 | 15 | 18 |
| 0.3% of Example 20 | — | 14 | 17 | 19 |
| 0.3% of Example 20 | 1.7% of B | 13 | 15 | 17 |
| 0.3% of Example 21 | — | 10 | 13 | 15 |
| 0.3% of Example 21 | 1.7% of A | 12 | 14 | 16 |

What is claimed is:

1. A titanocene of formula I

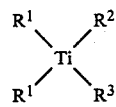     (I)

in which the two radicals $R^1$ independently of one another are cyclopentadienyl- which is unsubstituted or substituted by $C_1$–$C_{18}$-alkyl, $C_2$–$C_{18}$-alkenyl, chlorine, phenyl or cyclohexyl, wherein, in this titanocene, at least one radical $R^1$ is cyclopentadienyl- which is substituted by at least one group of formula IV or formula V $(R^6)_3Z-$     (IV)

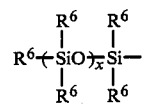     (V)

in which Z is Si, x is 1, 2 or 3, and each radical $R^6$ independently is linear or branched $C_1$–$C_{18}$-alkyl, $C_1$–$C_4$-halogenoalkyl, phenyl, $C_1$–$C_{18}$-alkoxy or $C_1$–$C_{18}$-alkoxy or $C_1$–$C_{18}$-alkoxymethyl;

$R^2$ is a 6-membered carbocyclic or 5- or 6-membered heterocyclic aromatic ring which is substituted by F, $CF_3$, $C_2F_3$, $CF_2Cl$ or $CF_2CH_3$ in at least one of the two ortho-positions relative to the metal-carbon bond, or is furthermore substituted by one or more of the groups halogen, $C_1$–$C_{12}$-alkyl; $C_1$–$C_4$-alkoxy, $C_2$–$C_{10}$-alkoxycarbonyl, aminocarbonyl with up to 12 C atoms, or by a primary, secondary or tertiary amino or aminoalkyl group with up to 20 C atoms or a quaternary ammonium or ammonium alkyl group with up to 30 C atoms; or, when $R^2$ is an aromatic ring substituted by F, $R^2$ can be further substituted by at least one polyoxaalkylene radical which is free or etherified or esterified, said radical being bonded to the aromatic ring either directly or via a bridge group; or $R^2$ and $R^3$ together are a radical of formula III $-Q-Y-Q-$     (III)

in which Q is a carboxylic aromatic ring which is bonded to the titanium atom in the 2-position relative to the Y group and is substituted by fluorine in the 3-position, Y is methylene, $C_2$–$C_{12}$-alkylidene which is unsubstituted or substituted by phenol; $C_5$–$C_7$-cycloalkylidene, or Y is a group $-NR^5-$, $-O-$, $-S-$, $-SO-$, $-SO_2-$, $-CO-$, $-SiR_2^4-$ or $-SnR_2^4-$ where $R^5$ is hydrogen, $C_1$–$C_{12}$-alkyl, cyclohexyl, phenyl, tolyl or benzyl, and the radicals $R^4$ independently of one another are $C_1$–$C_{12}$-alkyl, cyclohexyl, phenyl or benzyl;

$R^3$ has one of the meanings given for $R^2$, or $R^3$ is $C_2$–$C_{12}$-alkynyl. phenylalkynyl which has 2–5 C atoms in the alkynyl radical and is unsubstituted or substituted by halogen or $C_1$–$C_4$-alkyl in the phenyl radical; or $R^3$ is a group $-SiR_3^4$ or $-SnR_3^4$ in which radicals $R^4$ are as defined above; or $R^3$ is $-N_3$ or $-CN$; and when $R^2$ is an aromatic ring substituted by $-CF_3$, $-C_2F_5$, $-CF_2Cl$ or $-CF_2CH_3$, $R^3$ may also be halogen, $-NCO$ or $-NCS$.

2. A titanocene according to claim 1, wherein, in formula I, one radical $R^1$ is unsubstituted cyclopentadienyl and the other radical $R^1$ contains up to 3 substituents, or each radical $R^1$ is substituted cyclopentadienyl, at least one substituents corresponding to the formula IV or V.

3. A titanocene according to claim 1, in which x is 1 and Z is Si.

4. A titanocene according to claim 1, in which $R^6$ is $C_1$–$C_4$-alkyl, $C_1$–$C_4$-halogenoalkyl, $C_1$–$C_4$-alkoxy or phenyl.

5. A titanocene according to claim 1, in which, in formula IV, one radical $R^6$ is $C_1$–$C_{18}$-alkyl, $C_1$–$C_4$-halogenoalkyl, $C_1$–$C_4$-alkoxy or phenyl and the other two radicals $R^6$ are methyl.

6. A titanocene according to claim 1, in which the group of the formula IV is trimethylsilyl.

7. A titanocene according to claim 1, in which one radical $R^1$ is a-cyclopentadienyl anion substituted by a group of the formula IV or V and the other radical $R^1$ has the same meaning or is a cyclopentadienyl or methylcyclopentadienyl anion.

8. A titanocene according to claim 1, in which $R^2$ and $R^3$ in formula I are identical and are a 6-membered carbocyclic or 5- or 6-membered heterocyclic aromatic ring which is substituted by F in one or both of the ortho-positions relative to the metal-carbon bond or by $CF_3$, $C_2F_5$, $CF_2Cl$ or $CF_2CH_3$ in one ortho-position or said ring additionally containing substituents as defined in claim 1.

9. A titanocene according to claim 1, in which $R^2$ and $R^3$ are 2,6-difluorophen-1-yl, or said 2,6-difluorophen-1-yl containing 1 to 3 substituents as defined in claim 1.

10. A titanocene according to claim 9, in which $R^2$ and $R^3$ are a radical of the formula

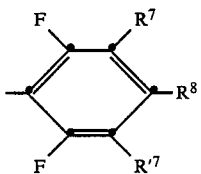

in which $R^7$, $R'^7$ and $R^8$ independently of one another are H, F, Cl or Br, or $R^7$ and $R'^7$ independently of one another are each H, F, Cl or Br, and $R^8$ is a primary, secondary or tertiary amino or aminoalkyl group with up to 20 C atoms or a quaternary ammonium or ammoniumalkyl group with up to 30 C atoms, or $R^8$ is a polyoxaalkylene radical which is free, esterified or etherified and is bonded to the phenyl ring directly or via a bridge group.

11. A titanocene according to claim 1, in which $R^2$ contains at least one polyoxaalkylene radical which is free, etherified or esterified and is bonded to the aryl radical directly or via a bridge group.

12. A titanocene according to claim 11, in which the polyoxaalkylene radical corresponds to the formula $$-C_zH_{2z}O)_oR^9,$$

in which z is a number from 2 to 6, o is a number from 1 to 20 and $R^9$ is H or $C_1$–$C_{18}$-alkyl.

13. A titanocene according to claim 1, in which $R^2$ is a radical of the formula

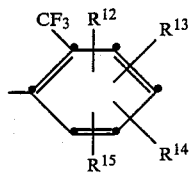

in which $R^{12}$, $R^{13}$, $R^{14}$ and $R^{15}$ independently of one another are hydrogen, $-CF_3$, bromine, chlorine or fluorine and $R^3$ has the meaning of $R^2$ or is halogen or $-N_3$, $-CN$, $-NCO$ or $-NCS$.

14. A titanocene according to claim 13, in which $R_{12}$, $R_{13}$ and $R_{14}$ are hydrogen and $R_{15}$ is in the ortho-position relative to the metal-carbon bond and is fluorine or hydrogen.

15. A titanocene according to claim 13, in which $R^3$ is F, Cl, Br, $N_3$, CN, NCO or NCS.

16. A titanocene according to claim 1, which is bis(-trimethylsilylcyclopentadienyl)-bis(pentafluorophenyl)-titanium, bis(trimethylsilylcyclopentadienyl)-bis[4-(1',4',7'-trioxaundecyl)-2,3,5,6-tetrafluorophenyl]-titanium, bis(trimethylsilylcyclopentadienyl)-o-trifluoromethylphenyl-titanium chloride or bis(trimethylsilylcyclopentadienyl)-bis[3-(1',4', 7'-trioxahendecyl)-2,6-difluorophenyl]-titanium.

17. A composition which is polymerizable by radiation and contains (a) at least one non-volatile monomeric, oligomeric or polymeric compound with at least one polymerizable ethylenically unsaturated double bond and (b) at least one titanocene of the formula I according to claim 1 as the photoinitiator.

18. A composition according to claim 17, which additionally contains at least one other photoinitiator (c).

19. A composition according to claim 18, which contains a benzil ketal, a 4-aroyl-1,3-dioxolane, a dialkoxyacetophenone, an α-hydroxy- or α-aminoacetophenone or a mixture thereof as component (c).

20. A coated substrate which is coated with a composition according to claim 17 on at least one surface.

21. A coated substrate which is coated with a composition according to claim 18 on at least one surface.

22. A process for the photographic production of relief images, which comprises exposing a coated substrate according to claim 20 imagewise and then removing the non-exposed portions with a solvent.

23. A liquid photoinitiator mixture containing a titanocene of formula I according to claim 1 and a photoinitiator selected from the group consisting of the benzil ketals, 4-aroyl-1,3-dioxolanes, dialkoxyacetophenones, alpha-hydroxyacetophenones, alpha-aminoacetophenones and mixtures thereof.

* * * * *